United States Patent
Li et al.

(10) Patent No.: US 9,121,807 B1
(45) Date of Patent: Sep. 1, 2015

(54) REAL-TIME MONITORING OF PLUTONIUM CONTENT IN URANIUM-PLUTONIUM ALLOYS

(71) Applicants: Shelly Xiaowei Li, Idaho Falls, ID (US); Brian Robert Westphal, Idaho Falls, ID (US); Steven Douglas Herrmann, Idaho Falls, ID (US)

(72) Inventors: Shelly Xiaowei Li, Idaho Falls, ID (US); Brian Robert Westphal, Idaho Falls, ID (US); Steven Douglas Herrmann, Idaho Falls, ID (US)

(73) Assignee: U.S. Department of Energy, Washington, DC (US)

(*) Notice: Subject to any disclaimer, the term of this patent is extended or adjusted under 35 U.S.C. 154(b) by 343 days.

(21) Appl. No.: 13/710,533

(22) Filed: Dec. 11, 2012

(51) Int. Cl.
*G01N 1/44* (2006.01)
*G01N 25/02* (2006.01)

(52) U.S. Cl.
CPC ..................... *G01N 25/02* (2013.01)

(58) Field of Classification Search
CPC .......... Y02E 30/38; G21C 3/02; G01N 25/00; G01N 1/44; G01N 25/02; G01N 25/486; G01N 33/00; G01N 2203/0222; G01N 33/227
USPC ........... 374/10, 11, 12, 14, 29, 16, 31, 32, 33, 374/34, 35, 36, 38, 39, 100, 141, 4, 5, 46; 422/51; 436/147; 376/261, 265, 416
See application file for complete search history.

(56) References Cited

U.S. PATENT DOCUMENTS

| | | | | |
|---|---|---|---|---|
| 2,778,730 A * | 1/1957 | Spedding et al. | ................. | 420/2 |
| 3,051,838 A * | 8/1962 | Culp, Jr. | ........................ | 250/392 |
| 3,063,923 A * | 11/1962 | Mayer | ........................... | 252/638 |
| 3,346,673 A * | 10/1967 | Last et al. | ..................... | 264/0.5 |
| 3,995,485 A * | 12/1976 | Beyer et al. | ..................... | 374/33 |
| 4,581,813 A * | 4/1986 | Terhune | ........................ | 376/247 |
| 4,684,265 A * | 8/1987 | Bourrelly et al. | .............. | 374/43 |
| 5,574,960 A * | 11/1996 | Yonezawa | ....................... | 423/11 |
| 7,611,903 B2 * | 11/2009 | Vogel et al. | .................... | 436/177 |
| 8,535,579 B2 * | 9/2013 | Heit et al. | ...................... | 264/0.5 |
| 2015/0098485 A1 * | 4/2015 | Pontillon et al. | ................ | 374/55 |

* cited by examiner

*Primary Examiner* — Gail Kaplan Verbitsky
(74) *Attorney, Agent, or Firm* — Michael J. Dobbs; Daniel D. Park; John T. Lucas

(57) ABSTRACT

A method and device for the real-time, in-situ monitoring of Plutonium content in U—Pu Alloys comprising providing a crucible. The crucible has an interior non-reactive to a metallic U—Pu alloy within said interior of said crucible. The U—Pu alloy comprises metallic uranium and plutonium. The U—Pu alloy is heated to a liquid in an inert or reducing atmosphere. The heated U—Pu alloy is then cooled to a solid in an inert or reducing atmosphere. As the U—Pu alloy is cooled, the temperature of the U—Pu alloy is monitored. A solidification temperature signature is determined from the monitored temperature of the U—Pu alloy during the step of cooling. The amount of Uranium and the amount of Plutonium in the U—Pu alloy is then determined from the determined solidification temperature signature.

19 Claims, 4 Drawing Sheets

REAL-TIME MONITORING OF PLUTONIUM CONTENT IN URANIUM-PLUTONIUM ALLOYS

GOVERNMENT INTERESTS

The United States Government has rights in this invention pursuant to Contract No. DE-AC07-05ID14517, between the U.S. Department of Energy (DOE) and the Battelle Energy Alliance.

FIELD OF THE INVENTION

The present invention relates to the in-situ monitoring of Uranium and Plutonium content of an alloy, preferably a nuclear fuel during processing or reprocessing.

BACKGROUND OF THE INVENTION

As new methods of processing nuclear fuel or reprocessing spent nuclear fuel are researched and eventually deployed, new methods for monitoring the fuel composition during a particular process are required for safety and to reduce proliferation risks. For example, during the reprocessing of spent fuel using a pyroprocessing technology, whereby the Pu in the spent fuel is collected together with some U as ingots of Uranium-Plutonium (U—Pu) alloy. The Pu content within the alloy may vary over a wide range depending on process conditions. Nevertheless, the International Atomic Energy Agency (IAEA) and other regulating entities need to verify the amount of Uranium and Plutonium precisely and in a timely manner. In addition, the real-time information of Pu content in the U—Pu alloy ingots is important for special nuclear material control and accountability. Current methods require sample extraction followed by expensive and time consuming analysis, which are plagued by sampling and analytical errors.

Therefore, there is a need for the real-time, in-situ monitoring of Plutonium content in U—Pu Alloys.

SUMMARY OF THE INVENTION

A method and device for the real-time, in-situ monitoring of Plutonium content in U—Pu Alloys comprising providing a crucible. The crucible has an interior non-reactive to a metallic U—Pu alloy within said interior of said crucible. The U—Pu alloy comprises metallic uranium and plutonium. The U—Pu alloy is heated to a liquid in an inert or reducing atmosphere. The heated U—Pu alloy is then cooled to a solid in an inert or reducing atmosphere. As the U—Pu alloy is cooled, the temperature of the U—Pu alloy is monitored. A solidification temperature signature is determined from the monitored temperature of the U—Pu alloy during the step of cooling. The amount of Uranium and the amount of Plutonium in the U—Pu alloy is then determined from the determined solidification temperature signature.

DETAILED DESCRIPTION OF THE INVENTION

Figure 1:
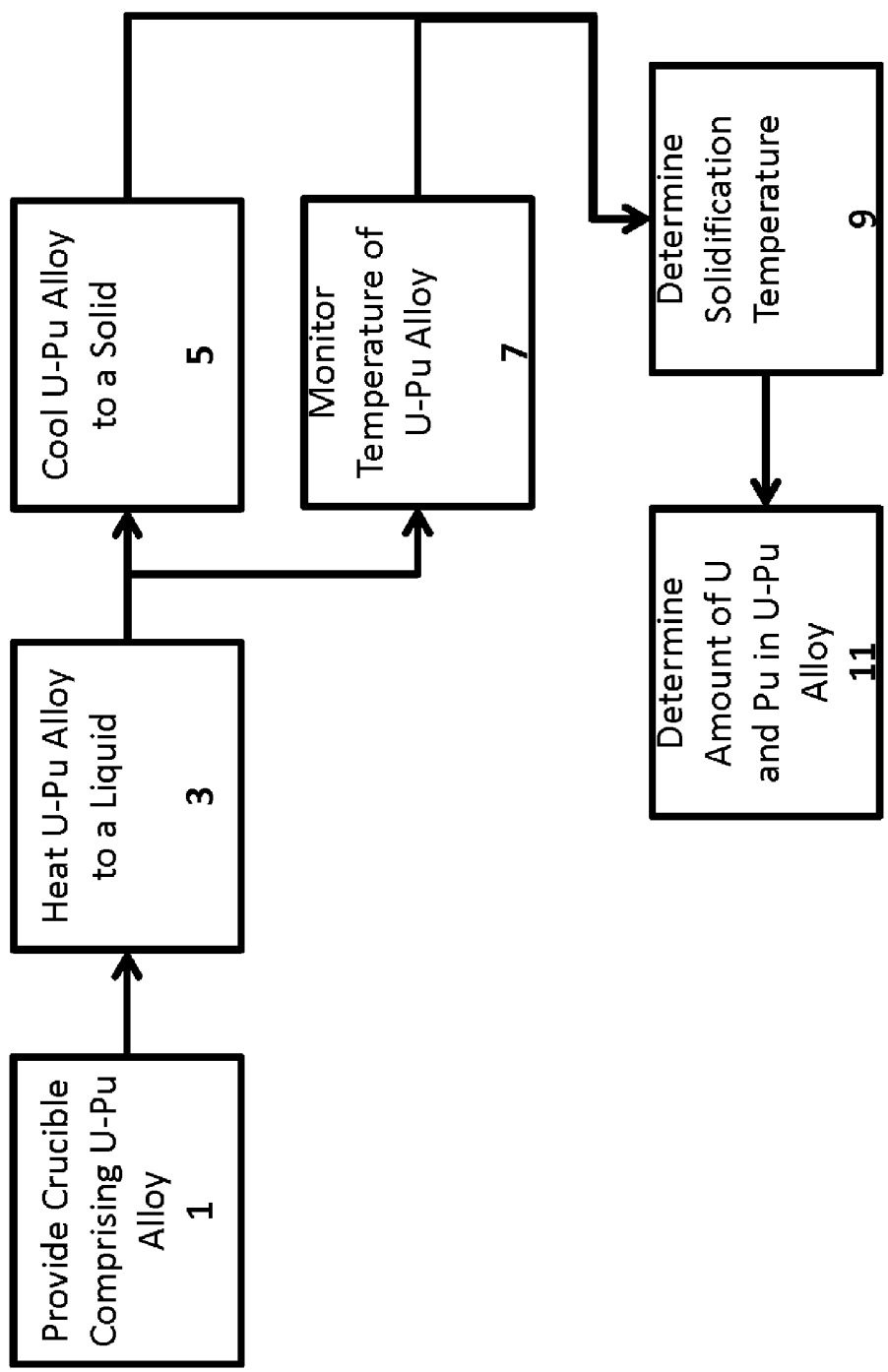
FIG. 1 depicts a flowchart of one embodiment of a method for the real-time, in-situ monitoring of Plutonium content in U—Pu Alloys.

FIG. 1 depicts a flowchart of one embodiment of a method for the real-time, in-situ monitoring of Plutonium content in U—Pu Alloys comprising providing a crucible 1. The crucible having an interior non-reactive to a metallic U—Pu alloy within said interior of said crucible. The U—Pu alloy comprises metallic uranium and plutonium. The U—Pu alloy is then heated to a liquid 3 in an inert or reducing atmosphere. The heated U—Pu alloy is then cooled to a solid 5 in an inert or reducing atmosphere. As the U—Pu alloy is cooled, the temperature of the U—Pu alloy is monitored 7. A solidification temperature signature is determined 9 from the temperature of the U—Pu alloy during the step of cooling. The amount of Uranium and the amount of Plutonium in the U—Pu alloy 11 is then determined from the determined solidification temperature signature.

Providing a Crucible 1

The crucible is any container having a melting point greater than the melting point of the U—Pu alloy. The crucible has an interior made of materials that are non-reactive to the metallic U—Pu alloy. A material non-reactive to the U—Pu alloy is any material that does not chemically, electrochemically or in any way which would degrade, change or reduce the amount of the material of the crucible. Preferably, the crucible is made of or has an interior surface comprising yttria. Preferably, the crucible comprises a configuration of one or more thermocouples that allows for continuous monitoring of temperature during the heating and cooling steps on the U—Pu alloy. The thermocouples are positioned to detect changes in alloy phases by either placement of the thermocouples in the melt or near the melt on the crucible. If placement of the thermocouples is on the crucible, then a correlation with the melt thermocouples is inferred, preferably accounting for any thermal losses and delays in heat transfer.

The U—Pu alloy comprises metallic uranium and plutonium, but may contain other elements, for example further comprising various amounts of Am, Np, Cm or combinations thereof, as well as other elements as impurities. The U—Pu alloy forms a continuous liquid-solid phase. The U—Pu alloy preferably consists essentially of Pu and U, whereby the amount of impurities does not significantly alter the thermal characteristic of the alloy. In one embodiment, various amounts of Am, Np, and Cm are present which may add an amount of uncertainty to the Pu and U measurements.

The steps of heating and cooling are performed in an inert or reducing atmosphere to prevent the oxidation of the U—Pu Alloy. For example, if the atmosphere was air, the U—Pu Alloy would be oxidized to uranium oxide and plutonium oxide, which would not only substantially increase the melting temperature, but would also change the composite melting point of the molten material. An inert atmosphere is any atmosphere which will not oxidize or reduce the U—Pu alloy within the normal operating temperatures of the U—Pu alloy. The normal operating temperatures of the U—Pu alloy are the various temperatures that the U—Pu alloy are normally exposed to within the crucible, preferably at least the melting and solidification temperatures of the U—Pu alloy, more preferably at least the melting and solidification temperatures of the U—Pu alloy plus or minus 50 degrees Celsius.

Heating the U—Pu Alloy to a Liquid 3

The U—Pu alloy is heated to a liquid in an inert or reducing atmosphere. As the exact melting point of the U—Pu alloy is not known, the alloy is preferably heated to a temperature at least 50 degrees Celsius greater than the melting point of pure uranium (1135° C.). The crucible is heated using one or more heat sources, preferably Joule heating, one or more burners, or a combination thereof. The heat sources are thermally connected to the U—Pu alloy, preferably through the crucible. Thermally connected means any connection which is capable of transferring heat, preferably a metal. In a preferred embodiment, one or more heat sources are placed around the crucible, which is thermally conductive.

Cooling the Heated U—Pu Alloy to a Solid 5

The U—Pu alloy is cooled to a solid. Preferably, the U—Pu alloy is cooled by at least a partial removal from one or more heat sources, or an application of one or more cooling sources. A cooling source is any means of cooling the U—Pu alloy, preferably one or more heat exchangers, heat pump, or combinations thereof. In a preferred embodiment, the cooling source is the natural dissipation of heat from the system while the heat sources are disabled. The cooling sources are thermally connected to the U—Pu alloy, preferably through the crucible. Thermally connected means any connection which is capable of transferring heat, preferably a metal. In a preferred embodiment, one or more cooling sources are placed around the crucible, which is thermally conductive.

Monitoring the Temperature of the U—Pu Alloy 7

During the step of cooling the heated U—Pu alloy to a solid, the temperature of the U—Pu alloy is monitored. Preferably, the temperature of the U—Pu alloy is measured directly using one or more temperature sensors, preferably one or more thermocouples. Preferably, one or more temperature sensors are used, preferably comprising one or more thermocouples. In other embodiments, one or more lasers, ultrasound detectors, thermometers, or other temperature measurements devices are employed to monitor the temperature of the U—Pu alloy directly or indirectly. In one embedment, one or more heat conductors are used to transfer heat to the one or more temperature sensor, thereby monitoring the temperature indirectly. In this embodiment, thermal losses between the U—Pu alloy 7 and the temperature sensors are accounted for in the subsequent calculations. This embodiment may be preferred depending on the heat of the U—Pu alloy and the maximum temperature of the temperate sensor.

As shown in FIG. 1, the monitoring of the U—Pu Alloy occurs during the cooling of the U—Pu alloy. Although, the monitoring of the temperature may be preferred in various embodiments for reasons other than the determination of the amount of U and Pu in the U—Pu alloy, it is not necessary for the determination of the amount of U and Pu in the U—Pu alloy.

Determining a Solidification Temperature Signature 9

A solidification temperature signature is determined from the temperature of the U—Pu alloy during said step of cooling. The temperature signature is data relating to the temperature of the U—Pu alloy over time recorded during at least one cooling step. Preferably, a plurality of the heating and cooling steps is performed to generate data including a plurality of cooling to solidification cycles, thereby increasing accuracy.

Determining the Amount of Uranium and the Amount of Plutonium 11

Once the solidification temperature is determined, the amount of Uranium and the amount of Plutonium in the U—Pu alloy is determined from the determined solidification temperature signature. As the U—Pu alloy will produce heat in its transition from a liquid to solid phases, the solidification signature can be used to determine the concentration of U and the concentration of Pu.

In one embodiment, a table of solidification temperatures and corresponding amount of Uranium and the amount of Plutonium is used. In this embodiment, the amount of Uranium and the amount of Plutonium that are in the U—Pu alloy are determined using known analysis techniques, preferably inductively-coupled plasma mass spectrometry (ICP-MS).

In a preferred embodiment, one or more inflections or plateaus in the solidification signature, produced by heat given off by the liquid to solid phase transition differing from the normal heat dissipation of the system, is used to determine the amount of Uranium and the amount of Plutonium in the U—Pu alloy. Preferably, in this embodiment, the first derivative of the temperature versus time of the U—Pu alloy during cooling is used to determine the inflection point, thereby determining the solidification temperature. Preferably, the solidification temperature is the temperature at which the first derivative of the temperature of the U—Pu alloy shows significant deviations, more preferably the temperature at which the first derivative is closest to zero. It should be noted that depending on the frequency of data, the first derivative may not actually hit zero.

Once the solidification temperature is determined, the U—Pu phase diagram is used to determine the amount of Uranium and the amount of Plutonium in the U—Pu alloy. Preferably, the phase diagrams are produced experimentally or from existing sources such as from ASM International, for example Pu—U phase Diagram (1994 Okamoto Y.); ASM International Diagram 905419, Am—Pu—U Phase Diagram (1993 Ogawa T.) ASM International 2006 Diagram 1200678, hereby fully incorporated by reference. Okamoto et al., "Investigation of the Pu—U Phase Diagram", J. Alloy Comp., 213/214 (1994), 372 describes an investigation of the Pu—U phase diagram, as well as a phase diagram generation technique that could be used for other alloys, hereby fully incorporated by reference.

Preferably, any calculations, lookups or other steps necessary to determine the amount of Uranium and the amount of Plutonium in the U—Pu alloy is performed by a control system without user calculation. In this embodiment, the control system comprises a computer, ASIC (application specific integrated circuit), microcontroller or other electronic device. In a preferred embodiment, the control system is a ATMEGA128 microcontroller as sold by ATMEL.

FIG. 2

Figure 2:
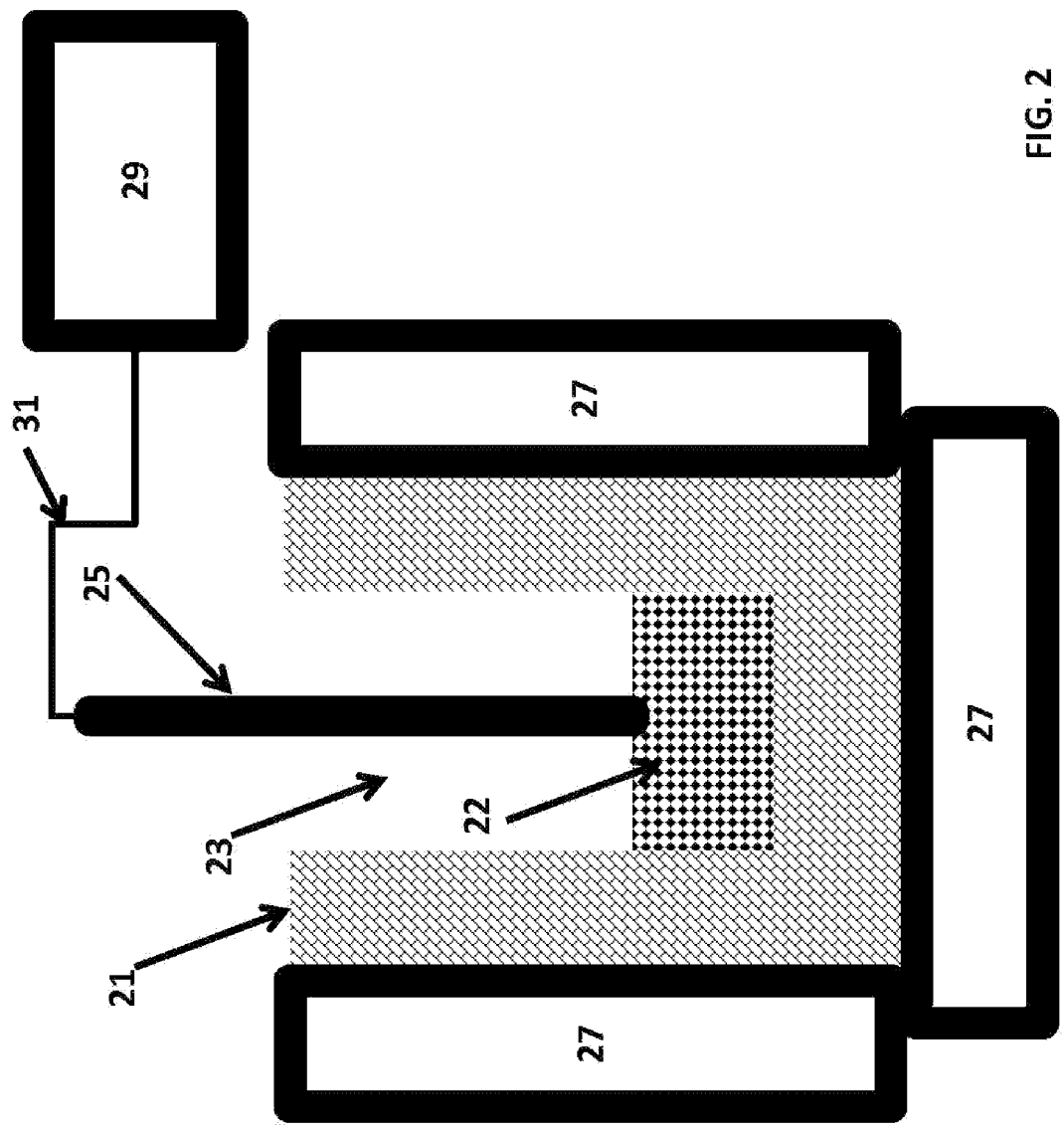
FIG. 2 depicts a cross-section view of one embodiment of a device for the real-time, in-situ monitoring of Plutonium content in U—Pu Alloys.

FIG. 2 depicts a cross-section view of one embodiment of a device for the real-time, in-situ monitoring of Plutonium content in U—Pu Alloys. As shown in FIG. 2, the crucible 21 has an interior 23 non-reactive to the metallic U—Pu alloy 22. In the embodiment shown in FIG. 2, one or more temperature sensors 25, preferably comprising any number of thermocouples allows for continuous monitoring of temperature during the cooling steps on the U—Pu alloy 22. The temperature sensors 25, as described above, are connected to a control system 29 via one or more temperature sensor wires 31. In alternate embodiments, the one or more temperature sensors 25 are connected via a communications means, for example radio frequency (RF), light transmission, sound, or a combination thereof. One or more heat sources 27, preferably using Joule heating, one or more burners, or a combination thereof, are preferably positioned around the crucible 21. Preferably, the heat sources are at least monitored, more preferably controlled by the control system 29. Although three heat sources 27 are depicted in FIG. 2, any number of heat sources 27 in various arrangements may be used. Preferably, the method of cooling the heated U—Pu alloy is the disabling of the one or more heat sources 27 and the natural dissipation of heat from the system.

The crucible 21 is preferably in inert or reducing atmosphere to prevent the oxidation of the U—Pu Alloy. In one embodiment, the crucible 21 is sealed in another container that provides an inert or a reducing atmosphere. In an alternate embodiment, the crucible 21 is sealed with one or more seals and filled with inert or a reducing gas.

FIG. 3

Figure 3:
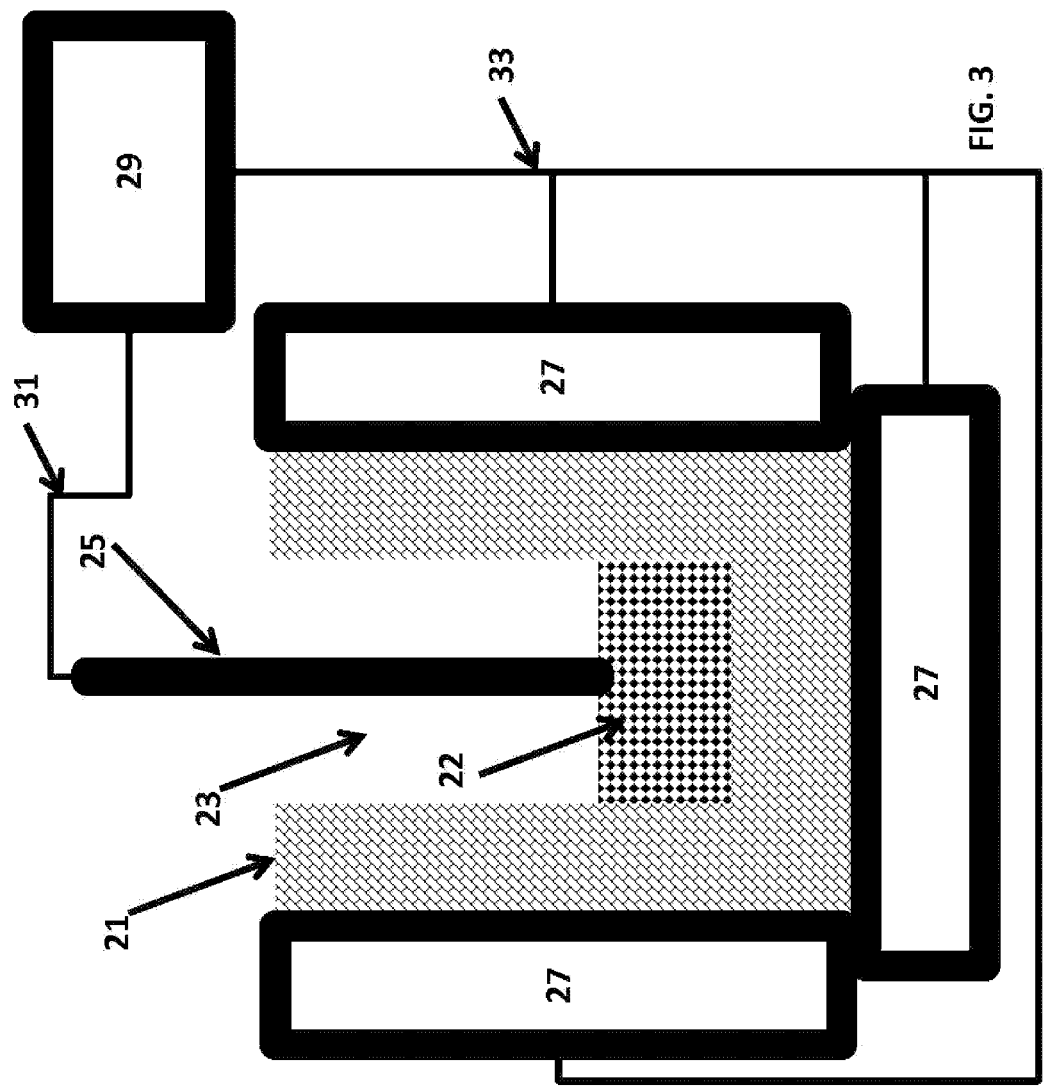
FIG. 3 depicts a cross-section view of one embodiment of a device used for the real-time, in-situ monitoring of Plutonium content in U—Pu Alloys comprising a control system connected to the heat sources.

FIG. 3 depicts a cross-section view of one embodiment of a device for the real-time, in-situ monitoring of Plutonium content in U—Pu Alloys comprising a control system connected to the heat sources. FIG. 3 is as described for FIG. 2 with the addition of the one or more heat sources 27 connected to the control system via one or more heat source wires 33. In alternate embodiments, the one or more heat sources 27 are connected to the control system 29 via a communications means, for example radio frequency (RF), light transmission, sound, or a combination thereof. Preferably, the heat sources 27 are at least monitored to determine whether they are enabled or disabled, more preferably controlled by the control system 29.

FIG. 4

Figure 4:
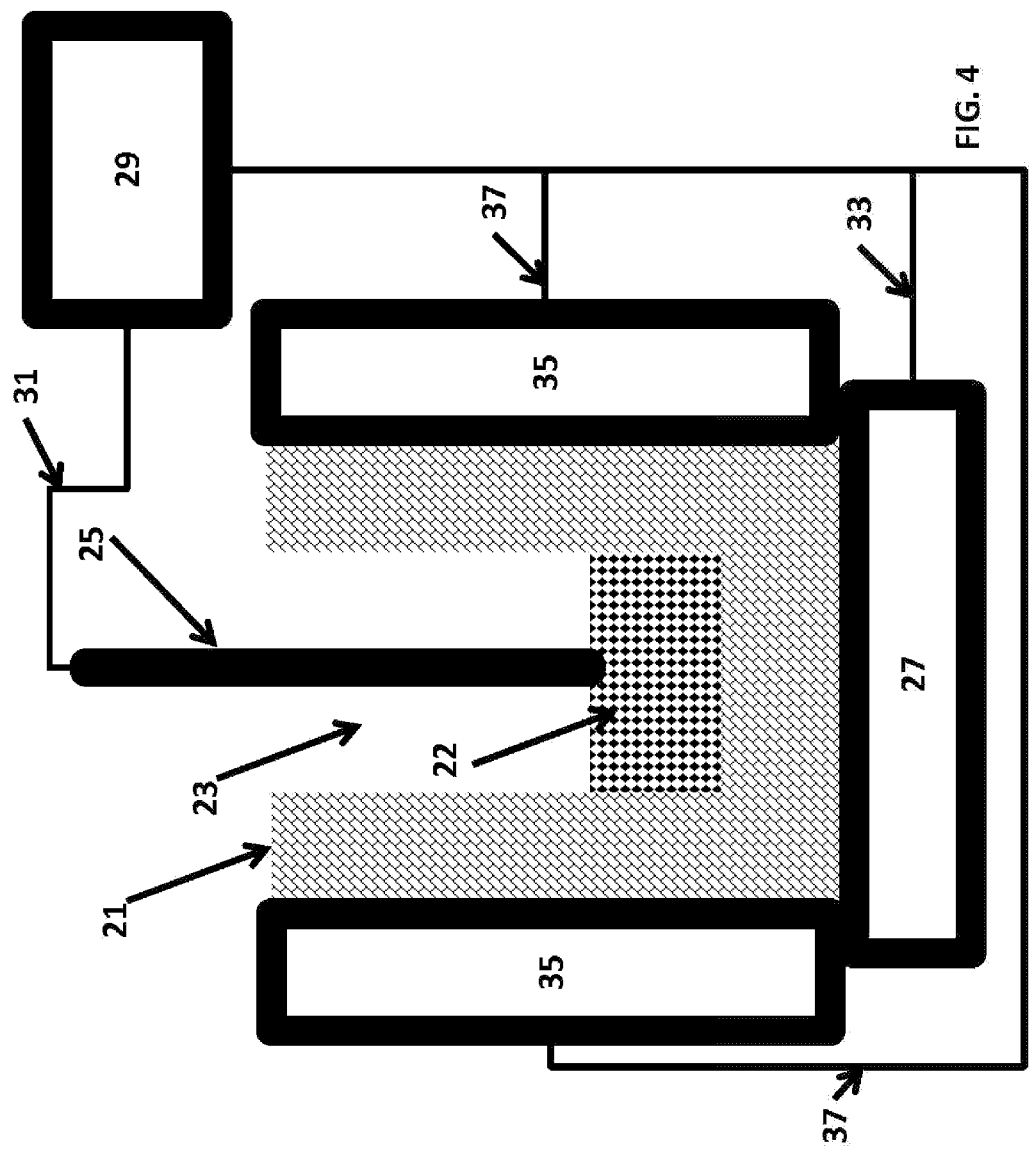
FIG. 4 depicts a cross-section view of one embodiment of a device used for the real-time, in-situ monitoring of Plutonium content in U—Pu Alloys comprising a control system connected to heat sources and cooling sources.

FIG. 4 depicts a cross-section view of one embodiment of a device used for the real-time, in-situ monitoring of Plutonium content in U—Pu Alloys comprising a control system connected to heat sources and cooling sources. FIG. 4 is as described for FIG. 3 with the addition of the one or more cooling sources 35 connected to the control system via one or more cooling sources wires 37. Preferably, the cooling sources are controlled by the control system 29. The cooling sources are as described above. In alternate embodiments, the one or more cooling sources 35 are connected to the control system 29 via a communications means, for example radio frequency (RF), light transmission, sound, or a combination thereof.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The invention claimed is:

1. A method for the real-time monitoring of Plutonium content in U—Pu Alloys comprising:
   a) providing a crucible; said crucible having an interior non-reactive to a metallic U—Pu alloy within said interior of said crucible; said U—Pu alloy comprising metallic uranium and plutonium;
   b) heating said U—Pu alloy to a liquid in an inert or reducing atmosphere;
   c) cooling said heated U—Pu alloy to a solid in an inert or reducing atmosphere;
   d) monitoring the temperature of said U—Pu alloy during said step of cooling said heated U—Pu alloy;
   e) determining a solidification temperature signature from said monitored temperature; and
   f) determining the amount of Uranium and the amount of Plutonium in said U—Pu alloy from said determined solidification temperature signature.

2. The method for the real-time monitoring of Plutonium content in U—Pu Alloys of claim 1 wherein at least said interior of said crucible comprises yttria.

3. The method for the real-time monitoring of Plutonium content in U—Pu Alloys of claim 1 wherein said step of heating said U—Pu alloy comprising heating said U—Pu alloy to at least 1185 degrees Celsius.

4. The method for the real-time monitoring of Plutonium content in U—Pu Alloys of claim 1 wherein said step of determining a solidification temperature signature comprises using a plurality of said temperature readings from a plurality of said step of heating and a plurality of said step of cooling.

5. The method for the real-time monitoring of Plutonium content in U—Pu Alloys of claim 1 wherein said step of heating comprises enabling one or more heat sources thermally connected to said U—Pu alloy and said step of cooling comprises disabling said one or more heat sources.

6. The method for the real-time monitoring of Plutonium content in U—Pu Alloys of claim 1 wherein said step of cooling comprises enabling a cooling means thermally connected to said U—Pu alloy.

7. The method for the real-time monitoring of Plutonium content in U—Pu Alloys of claim 1 wherein said step of determining the amount of Uranium and the amount of Plutonium in said U—Pu alloy from said determined solidification temperature signature comprises calculating a first derivative temperature versus time of the U—Pu alloy during said step of cooling to determine an inflection point.

8. The method for the real-time monitoring of Plutonium content in U—Pu Alloys of claim 7 wherein said determined inflection point is compared to a U—Pu phase diagram by intersecting the temperature and composition on the liquidus curve of the phase diagram.

9. The method for the real-time monitoring of Plutonium content in U—Pu Alloys of claim 1 wherein said U—Pu alloy consists essentially of metallic uranium and plutonium.

10. The method for the real-time monitoring of Plutonium content in U—Pu Alloys of claim 3 wherein U—Pu alloy consists essentially of metallic uranium and plutonium.

11. The method for the real-time monitoring of Plutonium content in U—Pu Alloys of claim 10 wherein:
   a) said step of heating said U—Pu alloy comprising heating said U—Pu alloy to at least 1185 degrees Celsius;

b) said step of determining a solidification temperature signature comprises using a plurality of said temperature readings from a plurality of said step of heating and a plurality of said step of cooling; and c) said step of determining the amount of Uranium and the amount of Plutonium in said U—Pu alloy from said determined solidification temperature signature comprises calculating a first derivative temperature versus time of the U—Pu alloy during said step of cooling to determine an inflection point.

12. The method for the real-time monitoring of Plutonium content in U—Pu Alloys of claim 11 wherein:

a) at least said interior of said crucible comprises yttria;

b) said U—Pu alloy consists essentially of metallic uranium and plutonium; and c) said determined inflection point is compared to a U—Pu phase diagram by intersecting the temperature and composition on the liquidus curve of the phase diagram.

13. The method for the real-time monitoring of Plutonium content in U—Pu Alloys of claim 12 wherein said step of heating comprises enabling one or more heat sources thermally connected to said U—Pu alloy and said step of cooling comprises disabling said one or more heat sources.

14. The method for the real-time monitoring of Plutonium content in U—Pu Alloys of claim 12 wherein said step of cooling comprises enabling a cooling means thermally connected to said U—Pu alloy.

15. A device for the real-time monitoring of Plutonium content in U—Pu Alloys comprising:

a) a crucible;

b) said crucible having an interior non-reactive to a metallic U—Pu alloy within said interior of said crucible;

c) one or more heat sources connected to said crucible;

d) a means for exposing the interior of said crucible to an inert or reducing atmosphere;

e) a means for cooling said crucible;

f) one or more temperature sensors thermally connected to the interior of said crucible;

g) a control system comprising a computer, ASIC (application specific integrated circuit), microcontroller or other electronic device;

h) said control system connected to said one or more heat sources;

i) said control system connected to said one or more temperature sensors;

j) said control system having a means for determining a solidification temperature signature of a U—Pu alloy within the interior of said crucible using one or more temperatures detected by said one or more temperature sensors; and k) said control system having a means for determining the amount of Uranium and the amount of Plutonium in said U—Pu alloy within said crucible from said determined solidification temperature signature.

16. The device for the real-time monitoring of Plutonium content in U—Pu Alloys of claim 15 wherein:

a) said means for cooling comprises a means for disabling said one or more heat sources;

b) said one or more temperature sensors comprises one or more thermocouples;

c) said heat sources heating said U—Pu alloy comprising heating the interior of said crucible to at least 1185 degrees Celsius;

d) said control system having a means for determining the amount of Uranium and the amount of Plutonium in said U—Pu alloy from said determined solidification temperature signature comprising:

i. using a plurality of said temperature readings from a plurality of said step of heating and a plurality of said step of cooling; and ii. calculating a first derivative temperature versus time of the U—Pu alloy during said step of cooling to determine an inflection point.

17. The device for the real-time monitoring of Plutonium content in U—Pu Alloys of claim 16 wherein:

a) at least said interior of said crucible comprises yttria; and b) said determined inflection point is compared to a U—Pu phase diagram by intersecting the temperature and composition on the liquidus curve of the phase diagram.

18. The device for the real-time monitoring of Plutonium content in U—Pu Alloys of claim 17 wherein said means for cooling comprises disabling said one or more heat sources.

19. The device for the real-time monitoring of Plutonium content in U—Pu Alloys of claim 17 wherein said means for cooling comprises one or more cooling sources thermally connected to said crucible.

* * * * *